(12) United States Patent
Wallis et al.

(10) Patent No.: US 6,907,107 B1
(45) Date of Patent: Jun. 14, 2005

(54) METHOD AND APPARATUS FOR THE ANALYSIS OF MATERIAL COMPOSITION

(75) Inventors: David J. Wallis, Malvern (GB);
Andrew M. Keir, Malvern (GB);
Martin T. Emeny, Malvern (GB)

(73) Assignee: QinetiQ Limited, London (GB)

( * ) Notice: Subject to any disclaimer, the term of this patent is extended or adjusted under 35 U.S.C. 154(b) by 0 days.

(21) Appl. No.: 09/936,560

(22) PCT Filed: Mar. 15, 2000

(86) PCT No.: PCT/GB00/00951

§ 371 (c)(1),
(2), (4) Date: Oct. 30, 2001

(87) PCT Pub. No.: WO00/55608

PCT Pub. Date: Sep. 21, 2000

(30) Foreign Application Priority Data

Mar. 16, 1999 (GB) ............................................... 9905953
Jan. 11, 2000 (GB) ............................................... 0000392

(51) Int. Cl.[7] ................................................. G01T 1/36

(52) U.S. Cl. ........................................... 378/83; 378/73

(58) Field of Search ............................ 378/70, 73, 82, 378/83, 85, 86, 88, 90, 72, 71, 84, 80

(56) References Cited

U.S. PATENT DOCUMENTS

| | | | |
|---|---|---|---|
| 4,144,450 A | | 3/1979 | Goebel |
| 4,575,922 A | | 3/1986 | Nemiroff |
| 4,928,294 A | | 5/1990 | Beard, Jr. et al. |
| 5,148,458 A | * | 9/1992 | Ruud ............................. 378/72 |
| 5,414,747 A | * | 5/1995 | Ruud et al. ..................... 378/73 |
| 5,457,727 A | * | 10/1995 | Frijlink ......................... 378/73 |

(Continued)

FOREIGN PATENT DOCUMENTS

| | | |
|---|---|---|
| DD | 270 770 | 8/1989 |
| EP | 0 186 924 | 7/1986 |
| EP | 0 354 045 | 2/1990 |
| GB | 2 166 630 | 5/1986 |
| GB | 2 169 480 | 7/1986 |
| GB | 2 289 833 | 11/1995 |
| WO | WO 97/12234 | 4/1997 |

OTHER PUBLICATIONS

C. Kittel, "Introduction to Solid State Physics" 3rd Edition (2nd printing), Nov. 1967, pp. 40–42.

A. Mazuelas et al, "Strain compensation in highly carbon doped GaAs/AlAs distributed Bragg reflectors" *Journal of Crystal Growth*, vol. 175/176, No. 3001, May 1997, pp. 383–386.

P. Velling et al, "InGaP/GaAs hole barrier asymmetry determined by (0 0 2) X–ray reflections and p–type DB–RTD hole transport" *Journal of Crystal Growth*, vol. 195, No. 1–4, Dec. 1998, pp. 117–123.

Primary Examiner—Edward J. Glick
Assistant Examiner—Hoon Song
(74) Attorney, Agent, or Firm—Nixon & Vanderhye P.C.

(57) ABSTRACT

A method is provided of analysing the composition of a semiconductor material (3) comprising irradiating the material with energy from an energy source (1) which energy is diffracted from the material, detecting one or more portions of the diffracted energy, and analysing the or each detected portion to obtain a parameter indicative of the intensity of the or each portion. The or each portion of the diffracted energy detected may be a quasi-forbidden reflection diffracted from the material, e.g. may be a (002) reflection diffracted from the material, or a (006) reflection. The detection of the or each portion of the diffracted energy may take place at one or more detection angles (9), or at all angles of reflection/transmission of the diffracted energy source, or at a range of angles around one or more detection angles. The energy source may comprise a beam of x-rays produced by an x-ray tube (2), and one or more detectors (4) may be used to detect the or each portion of the diffracted energy.

34 Claims, 6 Drawing Sheets

U.S. PATENT DOCUMENTS 5,530,732 A * 6/1996 Takemi ......................... 378/73
5,787,145 A    7/1998 Geus
6,072,853 A * 6/2000 Hall ............................ 378/73
6,577,705 B1 * 6/2003 Chang et al. ................. 378/45

* cited by examiner

METHOD AND APPARATUS FOR THE ANALYSIS OF MATERIAL COMPOSITION

This application is the U.S. national phase of international application PCT/GB00/00951, filed in English on 15 Mar. 2000, which designated the U.S. PCT/GB00/00951 claims priority to GB Application No. 9905953.7 filed 16 Mar. 1999 and GB Application No. 0000392.1 filed 11 Jan. 2000. The entire contents of these applications are incorporated herein by reference.

BACKGROUND OF THE INVENTION

1. Field of the Invention

This invention relates to a method and apparatus for the analysis of the composition of materials, and to the analysis of the composition of semiconductor materials using diffraction.

By "composition" it is meant the chemical composition.

2. Discussion of Prior Art

Many methods exist by which the chemical composition of a material may be analysed, e.g. characteristic x-ray emission or photoluminescence. Various diffraction methods of, for example, x-rays, electrons or neutrons also exist. In these the material lattice parameter (i.e. the spacing between lattice planes) is commonly measured. This can be related to the material composition by, for example using Vegard's law, and therefore the composition can be estimated from such measurements. However, a number of problems exist with this method. For some materials, e.g. SiGe, Vegards law is thought not to hold, and reliance on this to determine the composition can give rise to erroneous results.

It is desirable to be able to analyse the composition of semiconductor materials, e.g. III–V semiconductor materials, particularly III–V quaternary semiconductor materials. The wide variety of band gaps found in these compounds makes them suitable for the production of light emitting diodes and laser devices over a wide range of wavelengths. The ability to choose compounds with the desired band gaps and with minimal lattice mismatch to allow the growth of strain free structures offers considerable freedom to device designers. However, growth of quaternary III–V compounds with precisely controlled chemical compositions is very challenging, with a major limitation being the lack of a reliable and simple method for determining the chemical composition of these materials. The standard technique used to determine the composition of ternary III–V epilayers is measurement of x-ray diffraction rocking curves. This method utilises the x-ray rocking curve from a layer to determine its lattice constant which may then be related to the elemental ratios of the chemical elements present via a Vegard's law type relationship. For the case of quaternary compounds this technique does not provide a unique solution, since neither the group III or group V elemental ratios are known. Thus other techniques such as photoluminescence have traditionally been employed to provide additional information allowing quaternary compositions to be estimated. However, for such techniques the exact relationship between composition and band gap is often not known and effects such as compositional ordering also complicate interpretation. More direct techniques for compositional analysis, such as energy dispersive x-ray (EDX) analysis and wavelength dispersive x-ray (WDX) analysis, are also limited due to the strong spectral interference between many of the x-ray lines and their inability to measure thin and buried layers. This latter point is of particular importance in the case of Al containing layers which oxidise rapidly on exposure to air and must therefore be capped.

SUMMARY OF THE INVENTION

According to a first aspect the invention comprises a method of determining the relative amounts of different chemical elements E1 to En in the chemical composition of a crystalline semiconductor material, the method comprising diffracting a beam of radiation off the crystalline material and measuring the angle of at least one diffraction peak and the intensity of diffracted radiation at that diffraction angle, and using a processor to determine the relative amounts of the elements E1 to En in the chemical composition of the crystalline material by using values derived from the radiation scattering powers of the elements E1 to En and the position and intensity of said at least one diffraction peak.

The method also preferably comprises having the processor operate an algorithm that assumes the crystal lattice type to be a known predetermined kind (e.g. cubic, two layer repeat, or 3 layer repeat etc.).

According to a second aspect of the present invention there is provided a method of analysing the chemical composition of a semiconductor material comprising irradiating the semiconductor material with energy from an energy source which energy is diffracted from the semiconductor material so that diffracted energy is diffracted to a plurality of angles at an intensity dependent upon the angle, detecting one or more portions of the diffracted energy at a predetermined diffraction angle, or angles, and analysing the or each detected portion to obtain a parameter indicative of the intensity of the or each portion, and using the intensity-indicative parameter as a factor in determining the chemical composition of the semiconductor material.

The methods may comprise using a knowledge of the structure eg. crystal structure of the material, and the possible elements present in the material to determine the chemical composition of the material.

In practice it will usually be necessary to know the crystal structure and the possible elements present in the materials to be analysed. However, the position of the diffracted peak in diffraction space will tell you about the type of crystal structure and under special circumstances it may be possible to identify unknown elements using the intensity of a reflection.

The crystalline semi-conductor material may be assumed to be comprised of only a finite number of known predetermined chemical elements, and the processor may have operational in its processing of the measured input data and stored element scattering power values only the scattering powers for the known predetermined assumed finite number of elements that are assumed to be present. There may be other scattering power values in the stored element scattering power memory of the processor that are not operational for a selected finite combination of allowable expected chemical elements the ratios of which are to be determined. The material may be assumed to be comprised of four or less chemical elements.

Preferably the methods comprise determining the composition of a layer of a material and make use of a knowledge of the thickness of the layer. The methods may comprise determining the composition of a single layer of a material on a substrate of the material.

Preferably the methods comprise measuring the position of at least two diffraction peaks, or at least two portions of the diffracted energy, and using a knowledge of their position to determine the chemical composition. The methods may comprise measuring the intensity of a diffracted beam at least two positions or measuring the intensity of at least two portions of the diffracted energy and using this knowledge to determine the chemical composition.

The or each or some of the diffraction peaks, or the or each or some of the portions of the diffracted energy may be resultant from a (004) reflection.

The intensity of the or each or some of the diffraction peaks or the parameter indicative of the intensity of the or each or some of the portions of the diffracted energy may be normalised with reference to the intensity of the beam of radiation or the intensity of the energy from the energy source respectively. When the material comprises one or more layers on a substrate, the intensity of the or each of some of the diffraction peaks or the parameter indicative of the intensity of the or each or some of the portions of the diffracted energy may be normalised with reference to the intensity diffracted from the substrate.

The methods may comprise measuring the intensity of a single diffraction peak, or a single portion of the diffracted energy, and making use of a knowledge of the absolute intensity of the incident beam of radiation and the measured intensity to determine the chemical composition of the material. The methods- may comprise measuring the intensity of two diffraction peaks or two portions of the diffracted energy. One peak or portion may be diffracted from a layer of interest in a material, and the other peak or portion may be diffracted from a substrate of the material. The intensity peak or portion diffracted from the substrate may be used to calibrate or normalise the intensity peak or portion diffracted from the layer of interest.

In principle it is only necessary to detect the intensity of a single diffracted beam provided the absolute intensity of the incident beam is known. The composition of the layer may then be measured from the reflectivity of the sample. In practice however, it is simpler to measure the intensity diffracted from the substrate and use this to calibrate the intensity diffracted from the layer of interest. Thus usually, to measure the composition of a single layer on a substrate two peaks are measured and the intensity of both of them determined.

The intensity of the or each detected portion at different diffraction angles is related to the atomic structure, elemental constituents and thickness of the material. We have appreciated that a practical method of analysing the composition of a semiconductor material can be based upon the detection and analysis of a parameter indicative of the intensity of one or more portions of the diffracted energy. Using this method the measured composition of ternary zinc-blende and hexagonal and binary diamond cubic materials is directly dependant on the elemental species present, i.e. it does not rely on assumptions about the relationship between the composition and the lattice parameter, such as those contained in Vegard's law. It will be appreciated that the analysis of the chemical composition material is not usually to look for impurities, but rather to determine the relative amounts of certain predetermined alloy elements in the, typically crystalline, semiconductor material. For example, it may be known that elements X,Y and Z are substantially the only elements in the semiconductor, and the approximate ratios may, or may not, be known and the method evaluates the actual ratio of X:Y:Z.

Since making the present invention certain prior art has come to light including:—

U.S. Pat. No. 5,457,727 (Phillips) This discloses a way of detecting the interface between two layers of different materials and the composition of a layer. It uses grazing angle incidence of a beam to get grazing reflection from an interface (rather than diffraction from planes of atoms). In order to determine the composition Phillips need to know the refractive index of the material. They can either perform a separate experiment to measure it, or assume (or guess) it. Since n changes with strain state Phillips is not suitable for determining the composition of strained crystals, or crystals which have a varying degree of strain. Also it is unlikely to work with porous samples. If the refractive index of the material is known for sure this will be dependent upon the chemical composition of the layer and so knowledge of n is knowledge of chemical composition and so there is little point in performing the test to determine the composition.

GB 2 169 480 discloses a way of determining how much of a sample is present in the crystalline state, which is not the same thing at all as determining the chemical composition of a crystal.

GB 2 166 630 relates to polycrystalline samples and do not relate to determining the chemical composition of a semiconductor layer.

U.S. Pat. No. 5,414,747 (Ruud) relates to polycrystalline metal coatings, rather than single crystal or semiconductor layers. There is no realisation of the ability to be sensitive to chemical composition by detecting at quasi-forbidden angles.

Ruud does not relate to identifying the chemical composition of semiconductor crystals, nor how to make semiconductor wafers or devices. Ruud determines the composition of a polycrystalline metal layer in the sense of how much of the material is present in crystalline form vs. whole volume, the phase composition.

GB 2 289 833 (Mitsubishi) uses the traditional technique of lattice parameter determination by diffraction peak position. Although it discloses measuring the intensity of a diffracted beam at an angle it does not say what to do with it, and does not disclose using the intensity to evaluate the chemical composition of the semiconductor layer. Mitsubishi still rely on Vegard's law, even though they know the intensity.

U.S. Pat. No. 498,294 (U.S. Govt.) relates to imaging defects, not evaluating chemical composition of crystals.

U.S. Pat. No. 4,575,922 relates to detecting reflections. Although it measures the intensity of a diffracted beam it does not use it to determine chemical composition.

U.S. Pat. No. 4,144,450 (Siemens) relates to a powder diffractometer, not a single crystal, or semiconductor material, and although it measures an intensity at a peak it does not use it to determine chemical composition.

The material may be a multi-component semiconductor material. The material may be a ternary semiconductor material (i.e. have three elements in it). The material may be a binary semiconductor material. The material may be a quaternary semiconductor material. The material may be a quinternary material. The methods may further comprise measuring a parameter indicative of the lattice parameter of the quaternary semiconductor material, and using this and the parameter indicative of the intensity to provide, in a single diffraction measurement, an estimate of the composition of the material. The material may be a group IV semiconductor material such as those containing Si, Ge or C or combinations thereof. It may be a III–V semiconductor material, i.e. a compound comprising a combination of any number of group III elements and any number of group V elements. It may be a compound comprising a combination of any number of group II elements and any number of group VI elements. The material may be a III–V quaternary material, such as InAlAsSb, comprising two group III elements and two group V elements; or such as InPAsSb, comprising one group III element and three group V elements. The methods may comprise measuring a parameter indicative of the lattice parameter of the quaternary semiconductor material, and using this and the parameter indicative of the intensity to provide, in a single diffraction measurement, the ratio of the group III and the group V elements. As two pieces of information are required measurement of two parameters is necessary, e.g. measurement of the intensity and the lattice parameter of the material or parameters indicative thereof. The methods preferably provide an accuracy of better than 1% in the analysis of percentage composition of quaternary semiconductor materials. This is the level of control required over the growth of layers for the production of devices incorporating such materials. Normalisation and integration techniques may also be used, and should be robust to the effects of interference between features in the intensity due to for example the substrate and other layers of a material as these may produce peak overlaps.

For the semi-conducting materials of major interest the crystal structure is known and, in theory at least, each atomic element will only occupy specific sites within that crystal structure. Thus in a III–V material for example, all group III elements will occupy one lattice site and all group V elements will occupy the other. For a binary material such as GaAs which has the zinc-blende structure there are an equal number of lattice site for group III and group V elements and thus the Ga:As ratio is 1:1. If a second group V element such as Sb is added to GaAs to create a ternary compound this will displace some of the As on the group V lattice. However, the group III to group V ratio will remain 1:1. The uncertainty is therefore in the ratio of As:Sb. The standard way to measure this uncertainty is to measure the change in lattice parameter in the material caused by the addition of the larger Sb atoms. Our invention offers an independent way of determining the As:Sb ratio from the change in scattering strength due to the addition of Sb. Our invention also has the advantage that the scattering strength is not affected by strain, unlike the lattice parameter. In the case of a quaternary material eg. In GaAsSb again the group III to group V elemental ratio is assumed to be 1:1, but now the In:Ga and the As:Sb ratios are unknown. Measuring the lattice parameter of this material does not give a unique solution since it is possible to alter the In:Ga and As:Sb ratios without changing the lattice parameter. However, the present invention demonstrates that by using both the measured lattice parameter and the scattering strengths of the atoms it is possible to obtain both the In:Ga and the As:Sb ratios uniquely. In addition, it is possible that this idea may be extended to the case of quinternary materials, eg. InGaAlAsSb. Again, the group III to group V elemental ratio is assumed to be 1:1, but now the In:Ga, Al:Ga and As:Sb ratios are unknown. By making use of two different reflections and a measurement of the lattice parameter it should be possible to determine all three ratios.

The semiconductor material may be an alloy.

The methods may be used to analyse the composition of at least partially strained semiconductor materials. The methods are independent of the strain state of the semiconductor material for ternary zinc-blende and hexagonal and binary diamond cubic materials. For semiconductor materials comprising one or more layers deposited on a substrate, there may be a mismatch between any or all of the layers and the substrate due to the difference in their lattice parameters. Such differences may introduce a strain in the material. Indeed, other mechanisms may introduce strain into the material. It is necessary to know the strain state in order to rely on measurements of the lattice parameter to determine the material composition.

Since, in these methods, estimation of composition may be arrived at without knowledge of the lattice parameter, the need to know the strain by measuring the exact shape of the unit cell of the material is removed. Using known x-ray techniques for a cubic crystal a total of 8 double crystal rocking curves need to be measured to determine the shape of the unit cell, and therefore a time saving for collection of experimental data of the order of a factor of four to eight may be made using this method. Analysis of the composition using the methods of the invention may take of the order of two hours, whereas the prior art techniques can take about sixteen hours.

The semiconductor material may be a crystalline material, for example a cubic crystalline material. It may be a single crystal material, or a polycrystalline material or an amorphous material.

The semiconductor material may be doped. The methods may analyse the composition of doped semiconductor materials, e.g. alloys. This is particularly useful where the dopant levels are high enough to affect the lattice parameter but not sufficient to alter the diffracted energy. The material may be a solid, liquid or gaseous material.

The or each or some of the diffraction peaks or the detected portions of the diffracted energy may be at a quasi-forbidden angle of diffraction from the semiconductor material. For single component materials, i.e. comprised of one substance, beams diffracted to a certain angle from the material do not occur, i.e. are forbidden. For compound materials, i.e. comprised of two or more substances, such reflections may no longer be completely forbidden, i.e. are quasi-forbidden. Similarly for a two component crystal lattice there will be certain directions of diffraction where no, or substantially no, radiation is diffracted due to "cancellation" from the different atoms. Adding one, or two (or more) different atoms with different scattering power to the "host" crystal structure perturbs the forbidden diffraction angle and some radiation is diffracted at that angle after all because the alloyed/additional atoms contribute to diffraction in a slightly different way than do the atoms that they replace in the crystal structure. The or each or some of the quasi-forbidden diffraction may be at a (002) reflection or a (006) reflection.

The intensity of radiation diffracted at a quasi-forbidden angle (an angle that would be forbidden if the additional elements were not substituted for the basic lattice atoms at some sites) is very sensitive to the concentration/amount of alloyed/different atoms present—i.e. the chemical composition of the lattice. This is because the scattering power at a quasi-forbidden angle is related to the difference between the sum of the scattering powers of the main lattice atoms and the sum of the scattering powers of the substitute atoms, and this difference is sensitive to the relative number of each atom. The or each or some of the quasi-forbidden reflections for a zinc-blend lattice type may be a (002) reflection diffracted from the material, or a (006) reflection, or a combination of any of these reflections. For cubic crystalline semiconductor materials the (002) and the (006) reflections may have higher sensitivity to material composition than the (004) reflection. For example, the (004) reflection has an intensity proportional to the sum of the mean of the diffracting powers of the atoms in the (004) planes squared, whereas the (002) reflection has an intensity proportional to the difference of the mean of the diffracting powers of the atoms in the (002) planes squared. This latter is more sensitive to changes in the composition of the semiconductor material.

In cubic III–V quaternary semiconductor materials the (002) reflection intensity will depend on the difference in the diffracting powers squared of the group III and group V elements on the (002) planes. The methods may be used to analyse the composition of III–V quaternary semiconductor materials, such as InAlAsSb. The accuracy of the methods for composition measurement of this material may be assessed by using the zero Al content range of the "quaternary" InAsSb. This allows results to be compared with compositions calculated from a conventional mismatch approach, using the (004) reflection, thus providing an assessment of the errors involved in measuring composition from the intensity of a reflection. For the quaternary compound InAlAsSb the intensity of the (002) reflection is demonstrated to depend strongly on the group III ratio as expected due to the large difference in diffracting powers for In and Al.

The energy diffracted from the semiconductor material may contain various features, such as one or more intensity peaks. The or each or some of the portions of the diffracted energy detected may comprise an intensity peak. The parameter indicative of the intensity of the or each or some of the portions may be the integrated area of an intensity peak, or part of a peak. It may be the peak height, and/or the full width half maximum (FWHM) of the peak. Various techniques may be used to integrate the area, which may include use of Simpson's Rule or the Trapezium Rule, or fitting a function to a peak. Normalisation of the parameter may be carried out, for example by dividing by the total integrated intensity detected, or by dividing by the intensity of a diffracted peak of a reference sample. This is particularly useful when it is desired to compare the measured intensity with calculated values thereof.

Preferably an error in the region of or below 0.1% in the percentage composition of the material is achieved.

The detected portion or portions of the energy may be reflected from the material and/or transmitted through the material.

The method of the second aspect may comprise processing the or each or some of the portions of the diffracted energy before it is detected. One or more optical components may be used to process the or each portion. An analyser crystal may be used to process the or each portion. This acts to decrease the acceptance angle of a detector used to detect the or each portion, such that if two features in the diffracted energy overlap, these can be separated.

Detection of the or each portion of the diffracted energy may take place at all angles of reflection/transmission. Detection of the or each portion of the diffracted energy may take place at one or more detection angles. The intensity of the diffracted energy may not be uniform at all angles, but at certain angles may exhibit features such as peaks. The or each detection angle is preferably chosen such that a feature of the intensity is detected. When the energy is diffracted from a particular plane or set of planes e.g. the (002) planes of the material, this will not occur at only one angle but will be spread out over a range of angles due to, for example, the wavelength spread of the energy source, the angular diversion of the energy source, and the finite extent of the material. This range of angles may be a few are seconds up to 1000's are seconds depending on the material. The or each portion of the diffracted energy is preferably detected at a range of angles around one or more detection angles. The range of angles is preferably greater than or equal to the range of angles over which the diffracted energy from a plane or set of planes is spread.

One or more detectors may be used to detect the or each diffraction peak or the or each portion of the diffracted energy. These may be, for example, scintillation detectors, proportional counters, solid state detectors, films or a combination of any of these. Each detector will have a finite acceptance angle i.e. a range of angles of the diffracted energy which it can detect. The acceptance angle of the or each detector is preferably greater than or equal to the range of angles over which the diffracted energy from a plane or planes of a material is spread.

The methods may comprise determining the composition of a buried layer of the material using knowledge of the depth of the buried layer and the thickness of the buried layer.

It is essential to know both the depth of a buried layer and also the thickness of a layer in order to use the diffracted intensity to calculate a composition. This is because the intensity diffracted is also dependent on the depth and thickness of a layer. These parameters may be obtained from other features of the diffraction or measured simply using secondary techniques.

The or each portion of the diffracted energy may be detected at one or more angles by movement of the or each detector. Additionally or alternatively, the or each portion of the diffracted energy may be detected at one or more angles by the movement or rocking of the material. This latter produces a so called rocking curve. Additionally or alternatively, the or each portion of the diffracted energy may be detected at one or more angles by movement of the energy source.

Instead of using a substantially monochromatic energy source and moving the or each detector through a range of angles, the position of the or each detector may be fixed and the wavelength of the source changed. The position of the or each detector could also be moved in addition to changing the wavelength of the source.

The methods may further comprise measuring a parameter indicative of the lattice parameter of the material. This is preferably the angle of diffraction of the energy from the energy source, i.e. the angle between the reflected/transmitted portion of the energy and the planes in the material. Different layers within a material may have different plane spacings, due to for example a change in composition. Since the angle of diffraction of the energy is dependant on the lattice parameter the diffraction from individual layers of the material may be distinguished from other layers containing the same atomic species. Thus, the methods may be used to analyse the composition of buried layers, i.e. it has depth resolution. This is not possible using other techniques which measure composition directly since the signal from atoms outside the layer of interest can not be distinguished.

The beam of radiation or the energy source may comprise, for example, x-rays, electrons or neutrons. The or each wavelength of the beam or the energy source is preferably of the order of the lattice spacing of the semiconductor material to be analysed. Preferably, the stability of the intensity of the beam or source does not vary by more than 0.1% over the timescale of the analysis.

In a preferred embodiment a beam of x-rays is used to irradiate the semiconductor material. This may be produced by an x-ray tube. The x-rays may have one or more wavelengths, preferably in the range 0.5 angstroms to 2 or 3 angstroms. The x-rays may be substantially monochromatic, and may comprise one or more characteristic x-rays such as a K-alpha x-ray. One or more optical elements, such as one or more crystals or mirrors, may be used to partially monochromate and/or shape the beam.

The methods may be used to check the composition of a semiconductor material. The methods may further comprise comparing the detected composition of the material to a reference composition to determine if the detected composition is equal to or falls within a predetermined range around the reference composition, and producing a first output if the measured composition falls within the range and a second output if the measured composition falls outside the range. The first output may be a 'yes' output, and the second output may be a 'no' output. Such methods may be particularly useful to check the composition of a semiconductor material at the end of a semiconductor wafer production line. The check against a reference could be comparing the detected signals against allowable signals, or a range of allowable signals in a memory, or it could comprise actually conducting a diffraction test with a reference sample to generate the values against which the check is made. The methods could also be used to check the composition of a layer of a semiconductor material after deposition and before deposition of a subsequent layer. The methods may further comprise providing a signal depending on the comparison of the material composition to the reference composition. This may be fed back to the semiconductor material production process and used to change the process for the production of subsequent materials.

The methods may be used to test the validity of laws such as Vegard's law relating the lattice parameter and the composition of a semiconductor material. The methods may be used to analyse the composition of a material, and to further measure a parameter indicative of the lattice parameter of the material. The results may be compared to calculated results using e.g. Vegard's law to determine the validity of that law for that material.

According to a third aspect of the present invention there is provided an apparatus for the analysis of the composition of a semiconductor material being arranged to operate in accordance with the method of the first aspect of the invention.

The apparatus may comprise a diffractometer. The accuracy of measurement of the angle(s) of the detector in such an apparatus does not have to be as high as that in conventional diffractometers. Therefore the cost of such apparatus can be much reduced. Furthermore, if the diffractometer is designed to check that the composition of a semiconductor material/wafer is as it should be the detector(s) could be fixed, or movable between a limited range of positions, possibly under computer control. This may be cheaper to produce than a full freedom of movement diffractometer.

According to a fourth aspect of the present invention there is provided a composition measurement system arranged to analyse the composition of a semiconductor material according to the first aspect of the invention, and to compare this to a reference composition.

According to a fifth aspect of the present invention there is provided a method of analysing the composition of a multi-component material comprising irradiating the material with energy from an energy source which energy is diffracted from the material, detecting one or more portions of the diffracted energy, and analysing the or each detected portion to obtain a parameter indicative of the intensity of the or each portion.

According to a sixth aspect of the present invention there is provided a method of analysing the composition of a quaternary material comprising irradiating the material with energy from an energy source which energy is diffracted from the material, detecting one or more portions of the diffracted energy, and analysing the or each detected portion to obtain a parameter indicative of the intensity of the or each portion.

The method may comprise measuring a parameter indicative of the lattice parameter of the material and a parameter indicative of the intensity of diffraction of energy from an energy source from the material.

According to a seventh aspect of the present invention there is provided a method of analysing the composition of a single crystal of material comprising irradiating the crystal with energy from an energy source which energy is diffracted from the crystal, detecting one or more portions of the diffracted energy, and analysing the or each detected portion to obtain a parameter indicative of the intensity of the or each portion.

According to an eighth aspect of the present invention there is s provided a method of analysing the composition of an at least partially strained material comprising irradiating the material with energy from an energy source which energy is diffracted from the material, detecting one or more portions of the diffracted energy, and analysing the or each detected portion to obtain a parameter indicative of the intensity of the or each portion.

According to a ninth aspect of the present invention there is provided a method of analysing the composition of a material comprising irradiating the material with energy from an energy source which energy is diffracted from the material, detecting one or more portions of the diffracted energy at quasi-forbidden angles of diffraction, and analysing the or each detected portion to obtain a parameter indicative of the intensity of the or each portion.

According to a tenth aspect of the present invention there is provided a method of testing the validity of a law relating the lattice parameter and the composition of a semiconductor material.

The method may be used to test the validity of Vegard's law. The method may be used to analyse the composition of a semiconductor material, and to further measure a parameter indicative of the lattice parameter of the material. The results may be compared to calculated results using e.g. Vegard's law to determine the validity of that law for that material.

According to an eleventh aspect of the present invention there is provided a method of manufacturing a semiconductor chip comprising manufacturing a semiconductor wafer, analysing the composition of the wafer according to the method of the first aspect of the invention and etching the wafer to produce the chip.

BRIEF DESCRIPTION OF THE DRAWINGS

An embodiment of the present invention will now be described by way of example only, with reference to the accompanying drawings in which.

DETAILED DISCUSSION OF EMBODIMENTS

Figure 1:
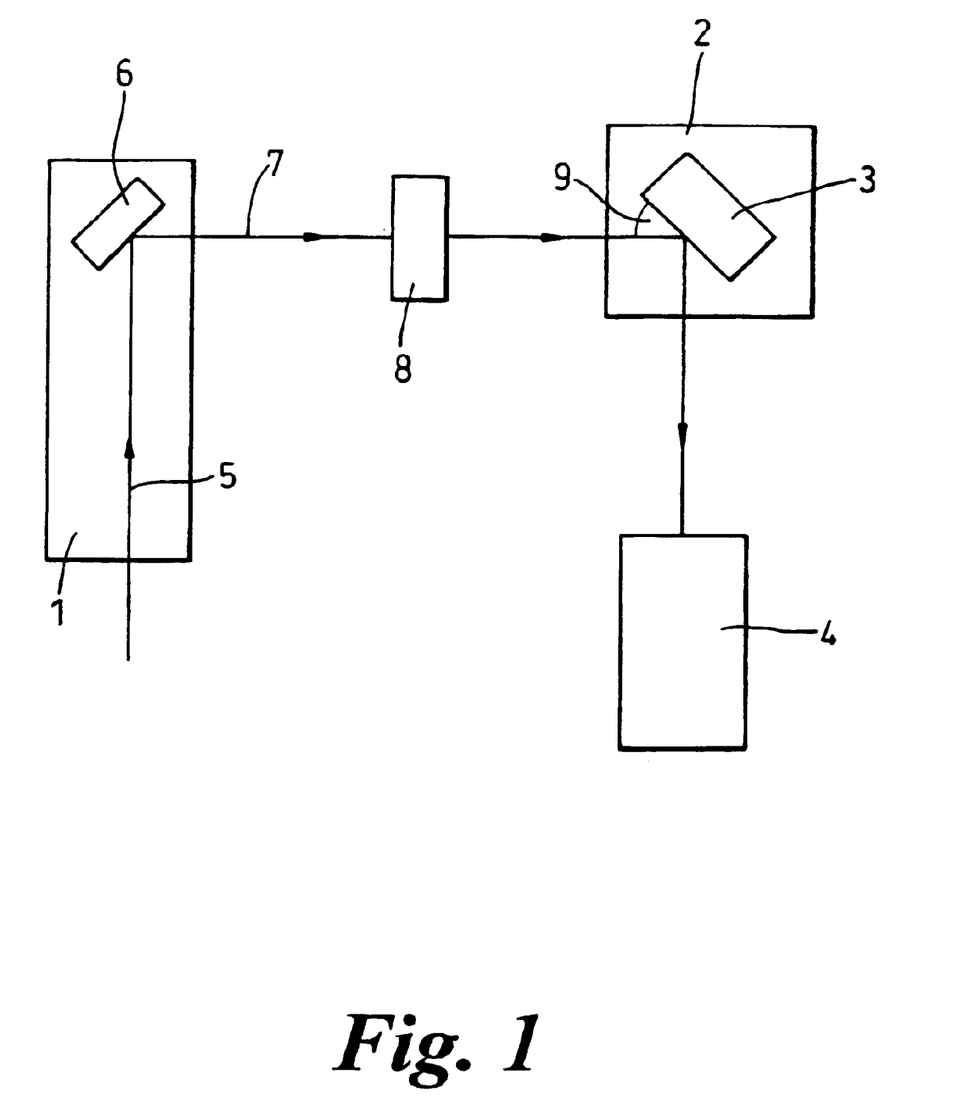
FIG. 1 is a schematic representation of an apparatus according to the second aspect of the invention.

The apparatus comprises a diffractometer having the general components shown in FIG. 1. The diffractometer may be a Bede scientific D3 high resolution diffractometer with a rotating anode source or a Bruker D5000 HR diffractometer operating with a standard sealed tube X-ray source and a Gobel mirror. Each comprises an x-ray source 1, a sample stage 2 on which a sample 3 of the semiconductor material to be analysed is mounted and a detector 4 for detecting the x-rays diffracted from the sample. The detector is a scintillation detector. The x-ray source comprises a beam of electrons 5 incident on a copper target 6 which produces a beam of characteristic x-rays 7. These are passed through an optical component 8 which acts to partially monochromates and shape the beam 7. The optical component is a Si (220) four reflection monochromator (Bede diffractometer), or a Ge (440) four reflection monochromator (Bruker diffractometer). These select a portion of the K-alpha1 characteristic x-ray for output. The resultant substantially monochromatic beam of x-rays is impinged on the sample, where it is diffracted. The size of the sample ranges from 100 microns to tens of mm wide. Such apparatus provide high photon counts and high source stability, allowing high quality data to be collected within reasonable counting times (approximately 2 sec per data point).

Rocking curves i.e. intensity versus angle 9, are measured by rocking the sample about its axis through a range of angles of approximately 800 arcsec. This allows extended data ranges to be collected to ensure that all features with significant intensity in the rocking curve are included to allow accurate normalisation of the data.

Quaternary and ternary semiconductor materials were used as samples. The quaternary and ternary epilayers were deposited in a VG V80H MBE system. The layers consisted of 200 nm of InAlAsSb or InAsSb deposited onto 2 inch InAs substrates at a growth temperature of 450° C. and a growth rate of 1.1 $\mu mhr^{-1}$. Since the quaternary sample is an Al containing compound a capping layer of 40 nm of InAs was also deposited onto all the structures to prevent oxidation of the layer in air. The presence of the capping layer also allows an assessment of the robustness of the composition measurements to the effects of thickness fringes from additional layers.

The measured rocking curves comprise a number of peaks corresponding to diffraction of the incident x-rays from the various layers of the samples and from the substrate. To analyse the composition of the samples, the intensity of the (002) quasi-forbidden reflections peak was assessed by integrating over a window centered on the highest point of the layer peak.

The strain state of the layers of the samples was estimated from the tetragonal distortion of the unit cell using the symmetric (004) reflection to give the lattice parameter perpendicular to the substrate surface and the asymmetric (444) reflection to give the lattice parameter parallel to the substrate surface. This analysis indicated that all the layers were 100% strained and therefore the estimate of composition derived from fitting the peak position of the (004) reflection should be unaffected by relaxation. The thickness of the layers was also confirmed by fitting the (004) rocking curve.

X-ray rocking curve simulations were carried out using commercial software RADS based on the Takagi-Taupin equations. These calculations give a full dynamical calculation of the diffracted intensity and take into account the beam conditioning optics.

In order to allow comparison of the intensities of calculated and experimental data, each measured rocking curve was normalised by dividing each point by the total integrated intensity under the rocking curve. Errors introduced by this procedure are negligible providing a large enough angular range of diffraction data is collected to ensure that the vast majority of x-rays diffracted from the (002) planes are detected.

The standard approach adopted for the extraction of experimental parameters from X-ray rocking curves is the simulation and fitting of the experimental data using full dynamical simulations. Whilst the calculations take into account, and reproduce effects such as "diffraction pulling" inadequacies in the theory in reproducing exactly the peak shapes due to, for example, not including the energy dispersion of the source and experimental problems such as noisy data and wafer curvature may strongly affect the accuracy with which data may be fitted. Additionally, the interference effects which occur due to additional layers in a structure such as Pendellosung or thickness fringes will cause problems in the measurement of peak intensities resulting from diffraction of a particular set of planes. In an effort to produce a data analysis method which is robust to these problems, the (002) quasi-forbidden reflection/diffraction peak intensity for the layers was integrated over a window centered on the highest point of the peak. Providing this integration window is suitably sized to include a significant fraction of the (002) intensity, but not so large as to include significant contributions from other structures in the rocking curve, the measured intensity should be relatively insensitive to the precise peak shape.

Figure 2:
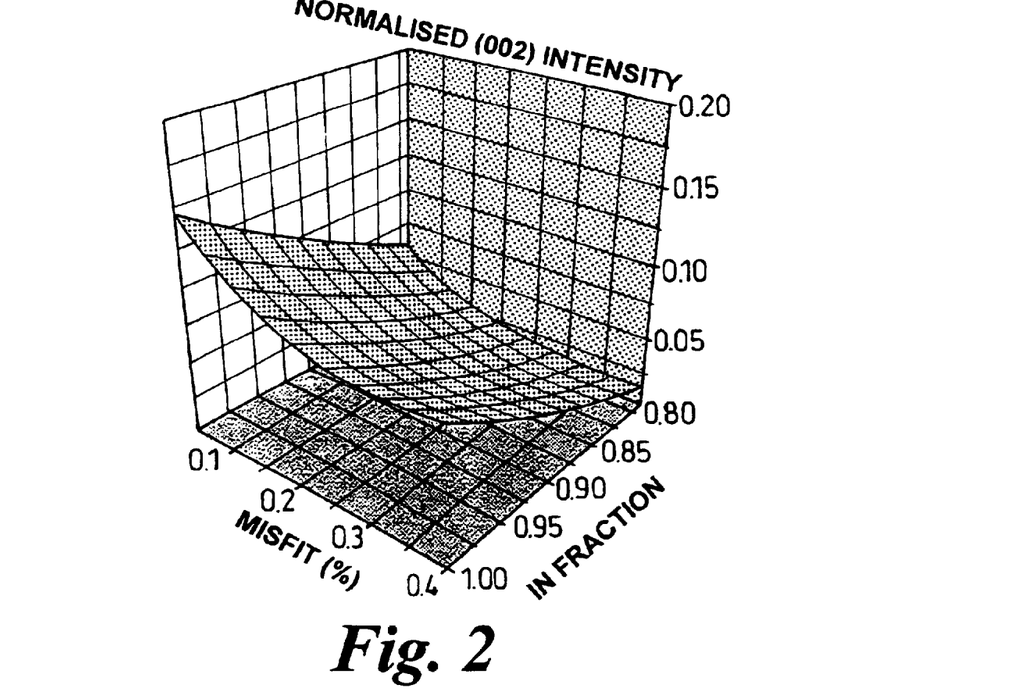
FIG. 2 is a 3-dimensional plot of the normalised (002) reflection intensity against misfit i.e. mismatch and In fraction for a 200 nm InAlAsSb layer on an InAs substrate with a 40 nm InAs cap.
Figure 3:
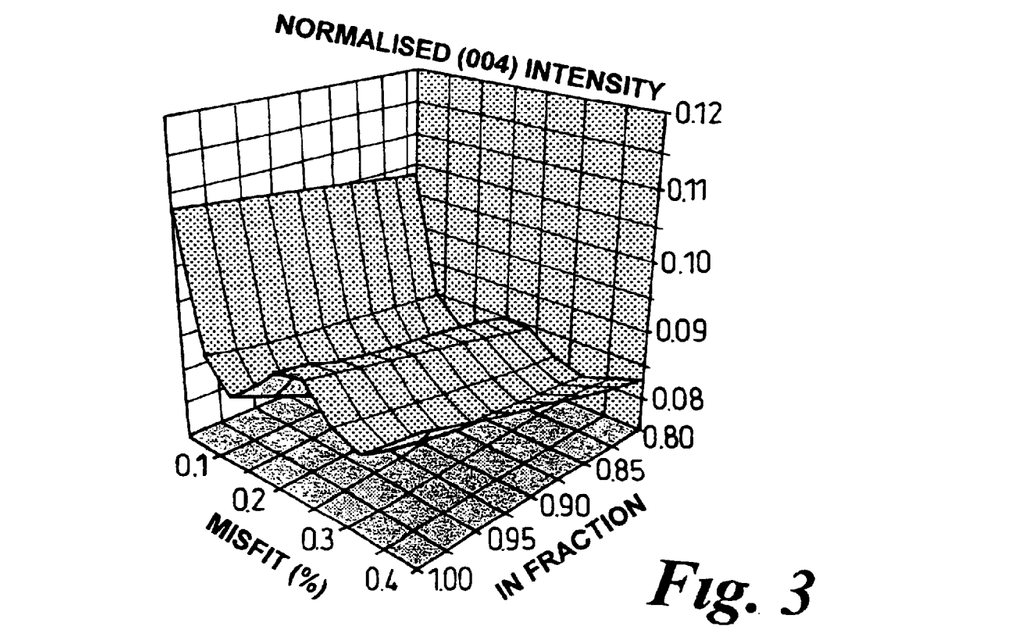
FIG. 3 is a 3-dimensional plot of the normalised (004) reflection intensity against misfit i.e. mismatch and In fraction for a 200 nm InAlAsSb layer on an InAs substrate with a 40 nm InAs cap.

FIG. 2 shows a 3-dimensional plot of the simulated and normalised (002) reflection intensity for an integration window of 50 arcsecs against In fraction and layer mismatch. As expected, a strong dependence of (002) intensity on the ratio of group III species is seen due to the large difference in diffracting powers between In and Al. For example, at a mismatch of 0.18% a 20% change in In fraction gives a change in (002) intensity of 75%. This compares to a change of only 6% in the simulated and normalised (004) intensity as seen in FIG. 3. Along the mismatch axis of FIG. 2 a major contribution to the variation in (002) reflection intensity results from the diffuse intensity around the diffraction peak from the substrate. This is seen as the strong increase of intensity at low mismatch. A contribution along the mismatch axis from the thickness fringes due to the 40 nm InAs cap included in these calculations is also seen as a slight rise in intensity at around 0.4% mismatch. This effect, due to thickness fringes, is much more obvious in the (004) reflection (FIG. 3). In this case, the displacement of the peak to approximately twice the angle between the substrate peak and the layer peak value of the (002) peak allows the inclusion of a whole oscillation of the thickness fringe along the mismatch axis.

Figure 4:
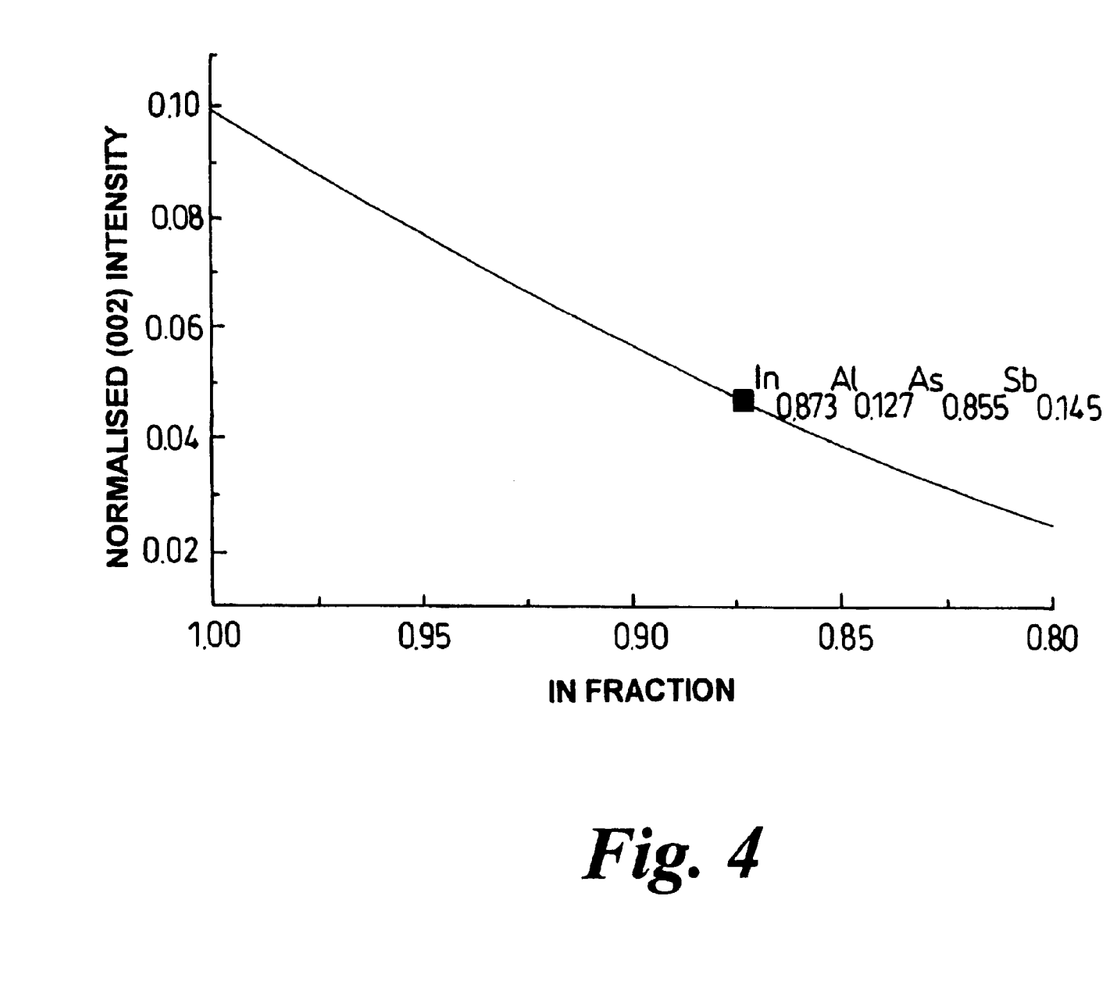
FIG. 4 is a 2-dimensional plot of the normalised (002) reflection intensity against In fraction taken from FIG. 2 at a misfit i.e. mismatch of 0.18%.

FIG. 4 shows a 2-D section taken from FIG. 2 at a mismatch value of 0.18% which corresponds to the measured mismatch for an InAlAsSb layer. Plotted on this graph is the measured, integrated intensity of the (002) peak for this layer using a 50 arcsec integration window. From this data, the composition of this layer is estimated as $In_{0.873}Al_{0.127}As_{0.855}Sb_{0.145}$. This value is in reasonable agreement with the composition, $In_{0.86}Al_{0.14}As_{0.85}Sb_{0.15}$, estimated from the mismatch of the layer and the group III fluxes measured from reflection high energy electron diffraction (RHEED) oscillations prior to deposition and assuming a sticking coefficient of one for the group III elements.

Figure 5A:
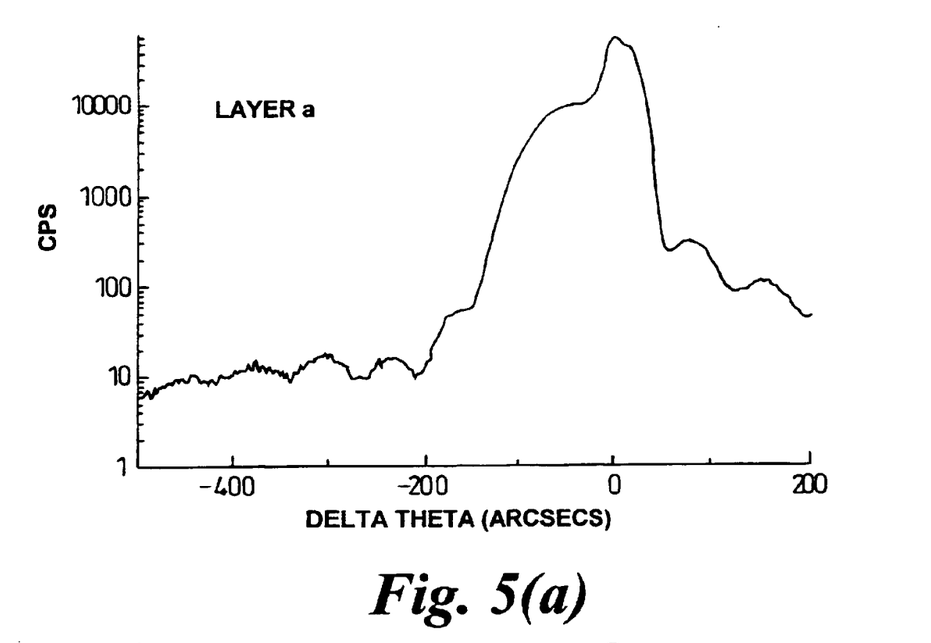
FIG. 5(a) is a plot of the double crystal rocking curve at the (002) reflections for a first layer, layer a of InAsSb.
Figure 5B:
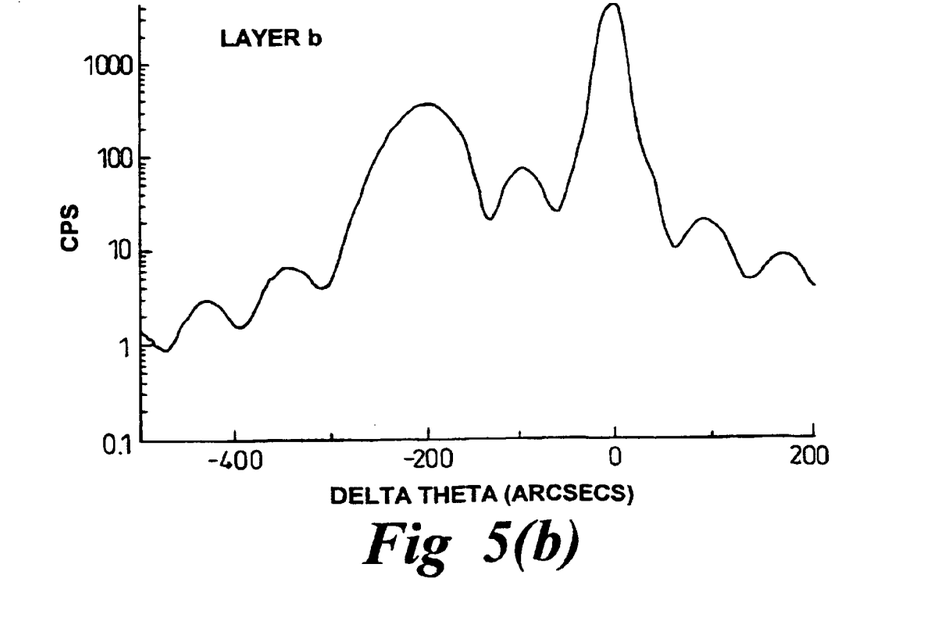
FIG. 5(b) is a plot of the double crystal rocking curve at the (002) reflections for a second layer, layer b, of InAsSb.
Figure 6:
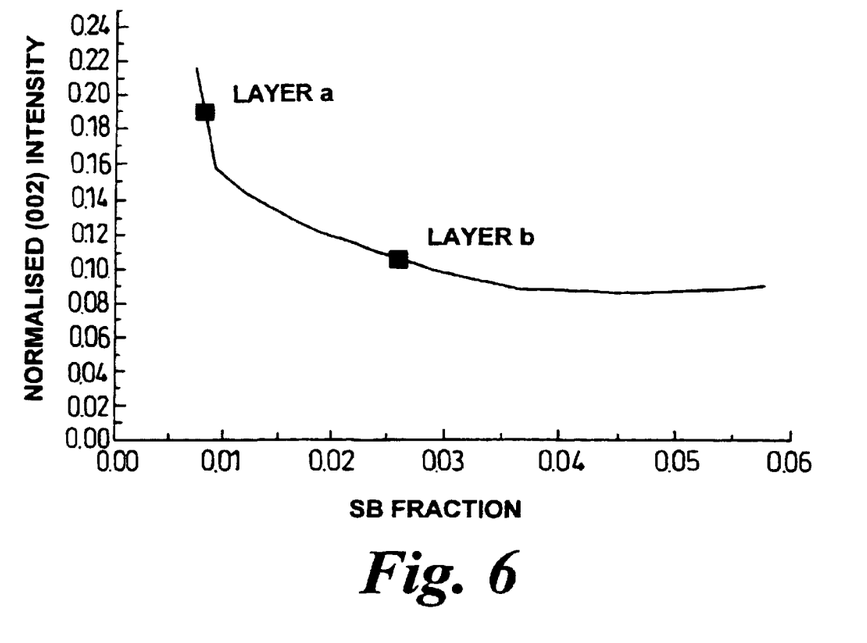
FIG. 6 is a plot of the normalised (002) reflection intensity taken from FIG. 2 and replotted against Sb fraction.

As previously discussed, accurate measurement of the composition of quaternary layers by other techniques is extremely difficult. Therefore, in order to obtain an estimate of the likely errors produced in matching experimental quasi-forbidden diffraction (002) intensities to the calculated (002) data, two fully strained InAsSb layers were grown. The double crystal rocking curves at the (002) reflections for these layers, layers a and b, are shown in FIGS. 5(a) and 5(b) respectively. FIG. 6 shows a 2-D plot taken from FIG. 2, of calculated (002) intensity for 100% In layers replotted against Sb fraction. This graph was then used to estimate compositions for the ternary layers shown in FIG. 5 and these values were compared to those determined using Vegard's law and the mismatch of the layers measured from their (004) reflections. Compositions of the InAsSb layers measured using the intensity of the (002) peaks were, $InAs_{99.2}Sb_{0.8}$ and $InAs_{97.4}Sb_{2.6}$ for layers a and b respectively. The compositions of these layers calculated using the standard x-ray technique were $InAs_{99.1}Sb_{0.9}$ for layer a and $InAs_{97.3}Sb_{2.7}$ for layer b. The difference between these two techniques is 0.1% for both layers. In the case of layer a, this degree of agreement is somewhat surprising in the light of the strong interaction between the (002) reflection and the substrate peak at very low mismatch as seen in FIG. 5(a). However, this good agreement demonstrates the robustness of the integration technique to changes in peak shape.

Figure 7:
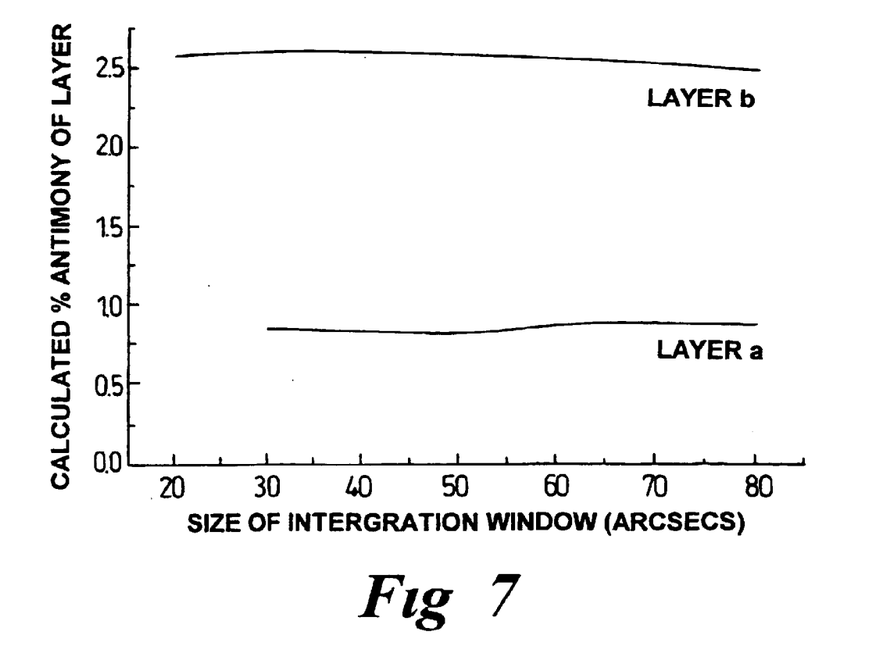
FIG. 7 is a plot of the calculated Sb fraction for the capped ternary layers a and b of the InAsSb against the size of the integration window used.

FIG. 7 shows a plot of how the calculated composition for layers a and b vary with different widths of integration window. This figure again demonstrates that this technique is relatively insensitive to the effects of interference between different features in the rocking curve. The largest deviation from the true composition of the layers measured from FIG. 6 is 0.2%. This occurs for the largest integration window which includes the tails of the (002) peaks and will thus contain significant contributions to the intensity from other sources.

Figure 8:
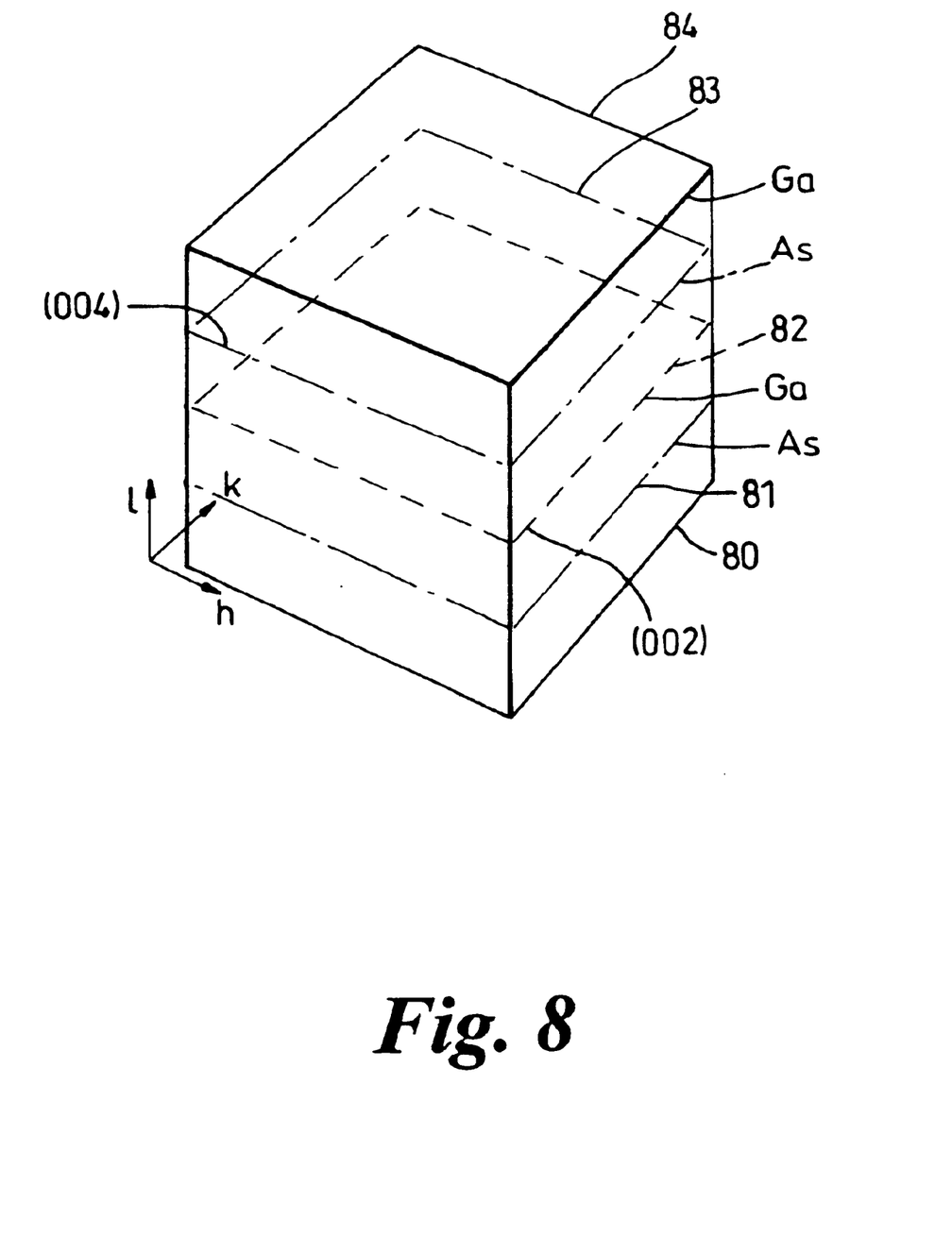
FIG. 8 is a schematic representation of a GaAs or InAs unit cell.

FIG. 8 shows a GaAs unit cell of a GaAs crystal lattice. With radiation incident at the correct Bragg angle, diffraction from the (004) planes has a strength that is strong because the scattering from plane 80, 81, 82, 83 and 84 are all in phase and additive: scattering from the planes of Ga atoms is in phase with the scattering from the planes of As atoms.

F or scattering from the 002 plane, referenced 82, the scattering from planes 80, 82 and 84 is in phase constructively, but the scattering from atoms in planes 81 and 83 are in phase with each other, but out of phase with that from planes 80, 82 and 84. Thus the intensity of scattered radiation in a particular direction is $\Sigma(f_1-f_2)^2$, where $f_1$ and $f_2$ are the scattering powers of Gallium ($f_1$) and Arsenic ($f_2$).

In a cubic cell with all atoms of the same material $\Sigma(f_1-f_2)=0$, because $f_1=f_2$. In a binary semiconductor alloy such as pure GaAs it is not zero, but is smaller than the signal from the (004) plane $\Sigma(f_1+f_2)^2$.

However, if some of the $f_1$'s and/or $f_2$'s are altered because the Ga and/or As are substituted for other alloy atoms (such as Al substituting Ga and Sb substituting As) then the $\Sigma(f_1-f_2)^2$ is altered significantly by relatively small changes in the concentration of atoms with different scattering powers than those of the primary lattice.

Similarly, in an InAs crystal when the In is substituted by Al, and/or As substituted by Sb it is possible to derive the Al/In and/or the As/Sb ratio by using information from the angle of scatter and the intensity of scatter to derive the chemical composition of the quaternary alloy.

It is envisaged that in the manufacture of semiconductor crystals there would be a machine set up to check that what was really being made was what was expected to be made by checking the chemical composition of the crystal using the present invention. It would therefore be known at what angle to measure a desired diffraction peak (whether that be the (002), (006), (004) or any other) and the detectors and x-ray emitter could be positioned in generally the correct places prior to a rocking test. The measurements of diffraction peak position/angle and intensity under the peaks would then be made and would produce a measured composition. The measured composition could be checked against an allowable range of compositions manually, or automatically by the computer. In one embodiment a computer controls the test and gives a "pass" or "fail" answer. Clearly, there is little point in a semiconductor chip manufacturer processing semiconductor wafers that are not of the correct predetermined chemical composition. If the wafer passes the control test subsequent manufacturing/processing steps are carried out on it.

The system may produce a print out of absolute concentrations/make up for a particular crystal or batch of crystals.

Protection for a data carrier carrying a program which in use controls apparatus in accordance with the present invention is required.

It will be appreciated that the invention, at least in one embodiment, allows the measurement of chemical composition of cubic quaternary and tertiary semiconductor alloys, especially III–V alloys, by making use of the intensity of quasi-forbidden angle diffraction, for example the (002) or (006) reflecting to determine the chemical composition of, for example, epilayers.

The invention allows the composition of a layer to be determined without any knowledge of the bulk lattice parameter of the tertiary phase. This can be useful when high purity bulk single crystals are not available, for example in the case of AlAs.

Compositions of crystals, such as quaternary compounds, can be determined by using a single x-ray measurement by making use of both the peak separation and peak intensities.

The technique allows composition determination in doped tertiary alloys where dopant levels are high enough to effect lattice parameters but not sufficient to alter the scattering strength. Thin and buried layers can be analysed.

It will be appreciated that the chemical composition can be determined in a single test, rather than having to test the material for other characteristics/parameters before determining the chemical composition. In comparison with the previous 8 double crystal rocking curves required in the prior art, the invention achieves a considerable time-saving in testing a sample.

What is claimed is:

1. A method of determining relative amounts of different chemical elements $E_1$ to $E_n$ in a chemical composition of a crystalline semiconductor material, the method comprising the steps of:
    diffracting a beam of radiation off said crystalline material;
    measuring an angle of at least one diffraction peak;
    integrating intensity of a portion of the diffracted radiation over a portion of said at least one diffraction peak located at said diffraction angle; and
    using a processor, determining the relative amounts of the elements $E_1$ to $E_n$ in the chemical composition of said crystalline material by using values derived from a radiation scattering powers of said elements $E_1$ to $E_n$ and the position and integrated intensity of said portion of said at least one diffraction peak.

2. A method according to claim 1 wherein at least some of said portions of said diffracted radiation is at a quasi-forbidden angle of diffraction from said semiconductor material.

3. A method according to claim 2 wherein some of said quasi-forbidden diffraction is at a (002) reflection.

4. A method according to claim 2 wherein some of said quasi-forbidden diffraction is at a (006) reflection.

5. A method according to claim 1 wherein at least some of said portions of said diffracted radiation is resultant from a (004) reflection.

6. A method according to claim 1 comprising using a knowledge of the structure of said material and the possible elements present in said material to determine the chemical composition of said material.

7. A method according to claim 1 wherein said crystalline semiconductor material is assumed to be comprised of only a finite number of known predetermined chemical elements and said processor has operational in its processing of the measured input data and stored element scattering power values only the scattering powers for the known predetermined assumed finite number of elements that are assumed to be present.

8. A method according to claim 7 wherein said material is assumed to be comprised of four or less chemical elements.

9. A method according to claim 1 comprising determining the composition of a layer of a material and making use either of (i) a knowledge of the thickness of said layer, or (ii) an assumption of the thickness of said layer being analyzed.

10. A method according to claim 1 comprising determining the composition of a single layer of a material on a substrate of said material.

11. A method according to claim 1 comprising either of (i) measuring the position of at least two diffraction peaks; (ii) measuring the position of at least two portions of the diffracted radiation; and using a knowledge of their position to determine the relative amount of chemical elements in the chemical composition of said semiconductor material.

12. A method according to claim 1 comprising either of (i) measuring the intensity of diffracted beams at at least two positions; (ii) or measuring the intensity of at least two portions of the diffracted radiation; and using this knowledge to determine the chemical composition of said semiconductor material.

13. A method according to claim 1 comprising measuring the intensity of either of (i) two diffraction peaks; (ii) two portions of the diffracted radiation.

14. A method according to claim 1 wherein said semiconductor material is a quaternary semiconductor material.

15. A method according to claim 1 wherein said semiconductor material is a ternary semiconductor material.

16. A method according to claim 14 further comprising either (i) measuring a parameter indicative of the lattice parameter of said quaternary semiconductor material; (ii) assuming a parameter indicative of the lattice parameter of said quaternary semiconductor material; and using this parameter and the intensity of either of (a) a diffraction peak, (b) the parameter indicative of the intensity; to provide, in a single diffraction measurement, an estimate of the composition of said material.

17. A method according to claim 1 wherein said semiconductor material is a III–V semiconductor material.

18. A method according to claim 1 wherein said composition of an at least partially strained semiconductor material is analyzed.

19. A method according to claim 1 wherein said semiconductor material is a single crystal material.

20. A method according to claim 1 wherein the percent of each chemical element of the chemical composition of said semiconductor material is analyzed with an error of 0.1% or below.

21. A method according to claim 1 which comprising measuring a parameter indicative of the lattice parameter of said semiconductor material.

22. A method according to claim 21 which is used to analyze the composition of a buried, non-surface, layer in the semiconductor material.

23. A method according to claim 1 comprising comparing the detected composition of said semiconductor material to a reference composition to determine if the detected composition is either (i) equal to that composition; (ii) falls within a predetermined range around the reference composition; and producing a first output if said measured composition falls within said range and a second output if said measured composition falls outside said range.

24. A method according to claim 1 including integrating said portion of the diffracted radiation over a region of said diffraction peak centered upon a point of maximum intensity of said diffraction peak.

25. A data carrier carrying a program which when running on detection apparatus is adapted to enable said apparatus to perform a method of claim 1.

26. Apparatus for the analysis of the composition of a semiconductor material being arranged to operate in use in accordance with the method of claim 1.

27. A composition measurement system arranged to analyze the composition of a semiconductor material according claim 1 and to compare this to a reference or output the results of the analysis.

28. A method of manufacturing a semiconductor chip comprising manufacturing a semiconductor wafer, analyzing the composition of said wafer according to claim 1 to test if it passes or fails a composition analysis test, and performing fabrication operations on said wafer to produce the chip if the wafer has a composition within predetermined parameters, and rejecting the wafer for further processing or fabrication operations if it has a composition outside of said predetermined parameters, rejected wafers not being subject to at least one processing step that they would have received had they passed.

29. A method according to claim 28 wherein wafers that pass said compositional analysis test and/or chips produced from such wafers are accompanied by data either confirming that they passed, or data giving details of their compositional analysis.

30. Chemical composition analysis apparatus comprising:
a sample holder,
a beam source,
at least one detector,
a controller, and
a processor, said controller being adapted to control said beam source and detector to direct a beam of energy onto a sample held in said sample holder and said at least one detector detects diffracted energy at diffraction angles, said at least one detector being coupled to said processor to provide said processor use with signals representative of the position of a diffraction peak and the intensity of said diffraction peak, and said processor being arranged to use said signal representative of the position of said diffraction peak and an integrated signal representative of the intensity of the diffraction peak over at least a portion thereof to evaluate the relative amounts of the predetermined chemical elements in the chemical composition of said sample.

31. Apparatus according to claim 30 having an element selection inputter adapted to enable a user to identify to said processor which chemical elements are to be assumed to be present in said sample to be analyzed, and therefore which chemical element scattering powers, or factor dependent upon the scattering powers, are to be used by said processor in determining the relative amounts of the chemical elements in the sample, said processor being adapted in use to operate with its processor on the measured input variables from said detector(s) and a subset of element scattering powers, or derived values, selected from a larger set of stored element scattering powers, or derived values, said subset being selectable by the operation of the element selection inputter.

32. Apparatus according to claim 30 wherein said sample holder, beam source and detector(s) are pre-set at predetermined positions relative to each other at a relationship where for a sample of a known kind said or at least one detector is disposed so as to detect at a quasi-forbidden diffraction angle.

33. Semiconductor wafer checking apparatus comprising apparatus according to claim 30.

34. A method of determining the relative amounts of different chemical elements $E_1$ to $E_n$ in the chemical composition of a crystalline semiconductor material, the method comprising diffracting a beam of radiation off the crystalline material and measuring the angle of at least one diffraction peak and the intensity of a portion of the diffracted radiation integrated over a window centered on the maximum peak intensity of said at least one diffraction peak located at said diffraction angle, and using a processor to determine the relative amounts of the elements $E_1$ to $E_n$ in the chemical composition of said crystalline material by using values derived from the radiation scattering powers of said elements $E1$ to $En$ and the position and integrated intensity of said window of said at least one diffraction peak.

* * * * *